United States Patent [19]

Brandman et al.

[11] Patent Number: 5,039,702

[45] Date of Patent: Aug. 13, 1991

[54] ALPHA-HALO-β-(SUBSTITUTED)THIOACRYLONITRILES AND THEIR USE FOR INHIBITING THE GROWTH OF MICROORGANISMS

[75] Inventors: Alyce Brandman, Glen Ridge; Milton Manowitz, Wayne; Albert I. Rachlin, Verona, all of N.J.

[73] Assignee: Givaudan Corporation, Clifton, N.J.

[21] Appl. No.: 339,322

[22] Filed: Apr. 14, 1989

Related U.S. Application Data

[63] Continuation-in-part of Ser. No. 160,872, Feb. 26, 1988, abandoned.

[51] Int. Cl.$^5$ .............................................. A01N 37/34
[52] U.S. Cl. ................... 514/526; 558/396; 558/438; 548/173; 548/189
[58] Field of Search ................ 558/438, 396; 514/520, 514/526

[56] References Cited

U.S. PATENT DOCUMENTS

| | | | |
|---|---|---|---|
| 2,231,838 | 2/1941 | Lichty | 260/464 |
| 2,913,479 | 11/1959 | Heininger et al. | 558/438 |
| 2,913,480 | 11/1959 | Heininger et al. | 558/438 |
| 2,919,224 | 12/1959 | Heininger et al. | 558/396 X |
| 2,919,225 | 12/1959 | Heininger et al. | 558/396 X |
| 3,050,545 | 8/1962 | Heininger et al. | 558/396 |
| 3,140,226 | 7/1964 | Stephens et al. | 514/520 |
| 3,188,342 | 6/1965 | Heininger et al. | 558/396 |
| 3,271,408 | 9/1966 | Frazza et al. | 558/438 X |
| 3,590,068 | 6/1971 | Toepfl et al. | 558/396 X |
| 3,659,006 | 4/1972 | Pande | 260/465.7 |
| 3,711,603 | 1/1973 | Baker | 71/67 X |
| 3,764,291 | 10/1973 | Baker | 71/67 |
| 4,238,408 | 12/1980 | Felix | 558/438 X |
| 4,647,687 | 3/1987 | Oeckl et al. | 71/67 |

FOREIGN PATENT DOCUMENTS

| | | |
|---|---|---|
| 0001312 | 4/1979 | European Pat. Off. |
| 0104432 | 4/1984 | European Pat. Off. |
| 186807 | 11/1966 | U.S.S.R. ............................ 514/520 |

OTHER PUBLICATIONS

"Webster's Third New International Dictionary", p. 1058 (1986), Merriam-Webster, Springfield, Mass.
IUPAC, "Nomenclature of Organic Compounds", (1979), p. 320.
Teijin, Ltd., C. A., 104:47177u (1986).
Abstract by Derwent of Japan Kokai Tokyo, J6 0078-902-A of May 4, 1985.
A. N. Kurtz et al., J. Org. Chem., 30, pp. 3141-3147, (1965).
W. H. Jura et al., J. Amer. Chem. Soc., 80, pp. 5402-5409 (1958).
B. Miller et al., Tetrahedron 23, pp. 1145-1152 (1967).

Primary Examiner—Joseph Paul Brust
Attorney, Agent, or Firm—Robert F. Tavares; Linda A. Vag

[57] ABSTRACT

Userful as antimicrobial agents in aqeuous systems are α-haloβ-(substituted)thioacrylonitriles of the formula

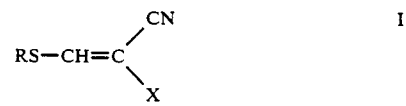

wherein X represents Cl, Br or I and R represents a lower alkyl, aryl, aralkyl, heterocyclo, or a thiocarbonyl group. The configuration about the double bond may be E or Z or a mixture thereof. These compounds provide effective control of microbial growth. The derivatives of formula I are economically prepared from acrylonitrile via a three-step process involving (a) halogenation, (b) dehydrohalogenation and (c) nucleophilic-type displacement. Except for those compounds wherein X is bromo and R is methyl or phenyl, the compounds of formula I are not mentioned in the prior art.

6 Claims, No Drawings

ALPHA-HALO-β-(SUBSTITUTED)THIOACRYLONITRILES AND THEIR USE FOR INHIBITING THE GROWTH OF MICROORGANISMS

This application is a continuation-in-part of application Ser. No. 07/160,872, filed Feb 26, 1988, now abandoned.

THE INVENTION

A number of aqueous systems are susceptible to microbial growth. Among these are latex paints, soaps, cutting oils, adhesives, cosmetic products, other oil and water emulsions, white water used in paper mills and water recirculated in industrial cooling towers and the like. The growth of bacteria and fungi in such systems can be a serious problem if not properly controlled. There is, consequently, a continuing need to provide effective and economical antimicrobial agents which protect these systems.

The antimicrobial agents of this invention are α-halo-β-(substituted)thioacrylonitriles of the formula

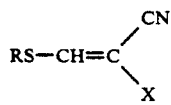

wherein X represents Cl, Br or I and R represents a lower alkyl, aryl, aralkyl, heterocyclo, or a thiocarbonyl group. The configuration about the double bond may be E or Z or a mixture thereof. These compounds provide effective control of microbial growth. Accordingly, the present invention provides a method of controlling microbial growth in an aqueous composition subject to spoilage thereby, which comprises incorporating in said composition an effective amount of a compound of formula I.

The derivatives of formula I are economically prepared from acrylonitrile (a readily available monomer widely used in the manufacture of plastics and polymers) via a three-step process involving (a) halogenation, (b) dehydrohalogenation and (c) nucleophilic-type displacement as illustrated below.

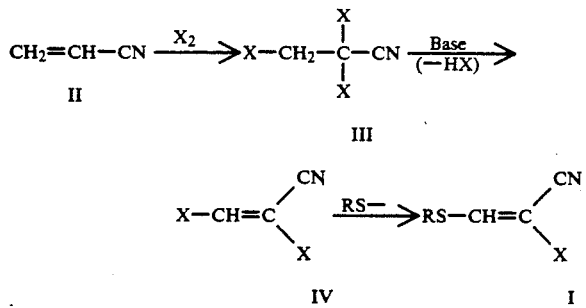

The acrylonitrile (II) is converted to the corresponding α,α,β-trihalopropanonitrile (III) by reaction with an appropriate halogenating agent such as chlorine, bromine or iodine, using methods known in the art. (See for example, J. G. Lichty, U.S. Pat. No. 2,231,838, Feb. 11, 1941.) The resultant trihalo derivative (III) is converted to the corresponding α,β-dihaloacrylonitrile (IV) via a dehydrohalogenation reaction using inorganic or organic alkaline reagents or other methods known in the art. (See for example, A. N. Kurtz et al., J. Org. Chem. 30, (1965) 3141–47.) Displacement of the halogen atom attached to the β-carbon can be accomplished using a nucleophilic sulfur anion derived from an appropriate mercaptan to yield the desired α-halo-β-(substituted)thioacrylonitrile (I). The methods, techniques and reagents used are similar to those known in the art. (See for example, B. Miller et al., Tetrahedron 23, (1967) 1145–52.) The acrylonitriles of formula I exist as a mixture of the E-and Z-isomers. Except for α-bromo-β-methylthioacrylo-nitrile and α-bromo-β-phenyl-thioacrylonitrile, the compounds of formula I are not mentioned in the prior art.

DESCRIPTION OF THE PREFERRED EMBODIMENTS

The term "lower alkyl" is to be understood to include straight or branched chain alkyl groups containing up to six carbon atoms, preferably one to four carbon atoms. The term "aryl" includes the usual aryl groups, in particular phenyl and naphthyl, which may contain one or more substituents such as halogen, lower alkyl, lower alkoxy, nitro, etc. The aryl portion of "aralkyl" is to be similarly interpreted, and the alkyl portion thereof is preferably a straight or branched chain alkyl group containing one to four carbon atoms. "Heterocyclo" embraces such groups which contain one or more oxygen, sulphur or nitrogen atoms as the ring heteroatom(s) and, may contain one or more ring carbonyls and/or fused benzene rings. The heterocyclic ring may be aromatic in character or at least partially saturated. The term "thiocarbonyl" is to be understood to include acyl groups derived from dithiocarboxylic acids by removal of the SH moiety. Suitable dithiocarboxylic acids include dithioformic acid, dithioacetic acid and further lower dithioalkanoic acids, dithiocarbamic acid, dimethyldithiocarbamic acid and further di-(lower alkyl)-dithiocarbamic acids. The thiocarbonyl group can be for example thioacetyl, thiocarbamoyl or dimethylthiocarbamoyl.

As illustrated above the compounds of formula I may be prepared by reaction of acrylonitrile with a halogenating agent such as elemental chlorine, bromine or iodine to yield the α,α,β-trihalopropanonitrile derivative (III). The halogenation reaction may be run with or without a solvent. If a solvent is used, it must be chosen from those solvents which are inert towards and do not react in any way with the halogenating agents. Such solvents would include but not be limited to ether, carbon tetrachloride, chloroform, methylene chloride and ethylene dichloride. For economical reasons it is preferred not to use a solvent.

The halogenation reaction may be carried out at 0°–80° C. Normally the reaction temperature is controlled by the boiling points of acrylonitrile (77° C.), the halogenating agent and/or the reaction solvent if a solvent is used. A reaction temperature of 10°–50° C. is preferred, with a reaction temperature of 25°–35° C. being especially preferred.

For economical considerations chlorine and bromine are the preferred halogenating agents. Chlorine is especially preferred due to its lower molecular weight (i.e., 71 g/mole for chlorine vs. 159.8 g/mole for bromine vs 253.8 g/mole for iodine), lower price, availability and greater ease in handling.

The α,α,β-trihalopropanonitrile (III) is converted to the corresponding α,β-dihaloacrylonitrile (IV) via a dehydrohalogenation reaction using an appropriate base. The base may be chosen from organic bases such as primary, secondary or tertiary amines (alicylic or acyclic), or heterocyclic bases such as pyridine, lutidine, quinoline, etc. The base may also be chosen from inorganic bases such as alkali metal carbonates or hydroxides. It is preferred to use an organic base due to their greater miscibility with the $\alpha,\alpha,\beta$-trihalopropanonitrile derivatives. Heterocyclic bases such as lutidine or quinoline are especially preferred.

It is preferred to carry out the dehydrohalogenation step using an organic base in the absence of a solvent. The reaction gives rise to the formation of an insoluble amine hydrohalide salt as a by-product, which is easily removed by filtration at the end of the reaction. If the use of a solvent is desired the solvent should be one which is not acidic or reactive with the organic or inorganic base being used to effect the dehydrohalogenation, and should be somewhat non-polar so as to render the by-product salt insoluble in the reaction medium. Such solvents would include but not be limited to ether, hexane, heptane, benzene, toluene, xylene, carbon tetrachloride, etc. It is especially preferred not to use a solvent since it simplifies product isolation and purification.

The dehydrohalogenation reaction can be suitably carried out at 20°-200° C. and is only limited by the boiling points of the starting material ($\alpha,\alpha,\beta$-trihalopropanonitrile), the product ($\alpha,\beta$-dihalocrylonitrile), the amine used and the solvent if one is used. A reaction temperature of 20°-180° C. is preferred, with a temperature of 40°-90° C. being especially preferred.

The $\alpha,\beta$-dihaloacrylonitrile (IV) can be converted to the corresponding $\alpha$-halo-$\beta$-(substituted)thioacrylonitrile (I) via a nucleophilic-type displacement of the halogen atom attached to the $\beta$-carbon atom by a sulfur anion derived from the appropriate mercaptan. The sulfur anion is most conveniently prepared in situ by reaction of a mercaptan with a strong base. Representative of mercaptans that can be used are alkyl mercaptans (either straight-chain such as methyl mercaptan, ethyl mercaptan, n-propyl mercaptan, etc., or branched-chain such as isopropyl mercaptan, isobutyl mercaptan, secondary butyl mercaptan, tertiary butyl mercaptan, etc.), aromatic mercaptans (e.g., thiophenol, para-chlorothiophenol), aralkyl mercaptans (e.g., benzyl mercaptan), heterocyclic mercaptans (e.g., 2-mercaptothiazole, 2-mercaptobenzothiazole), and dithiocarboxylic acids (e.g., dithioacetic acid, dithiocarbamic acid). The scope of this invention is not limited to the various mercaptans mentioned above, said list being merely representative of the general nature of the reaction.

The formation of the sulfur anion involves the removal of the acidic hydrogen atom bonded to the sulfur by an inorganic base such as the hydroxyl, alkoxyl, amide or hydride ion. The use of bases such as metal hydroxides or alkoxides involves the transfer of a proton to the conjugate base while the use of metal hydrides or amides involves the irreversible formation of ammonia or hydrogen gas. The use of the latter two bases (i.e., metal hydrides or metal amides) are less favored since they are more expensive, more hazardous and less amenable to large scale industrial processing. The base may also be chosen from organic bases such as primary, secondary or tertiary amines (e.g. triethylamine). The use of metal hydroxides and metal alkoxides are preferred with metal hydroxides, such as sodium hydroxide or potassium hydroxide being most preferred.

The sulfur anion can be prepared by adding the appropriate mercaptan to a solution of the base in an appropriate solvent. The choice of solvent may depend upon the base being used. With metal hydroxides or alkoxides the use of alcoholic solvents such as methanol, ethanol, isopropanol, propanol, etc. is desirable. When using metal alkoxides, the alcohol solvent must be anhydrous to prevent hydrolysis of the alkoxide to hydroxide. With metal hydrides and amides the choice of solvents is limited to aprotic, anhydrous solvents, such as ether, glyme, diglyme, tetrahydrofuran, etc. These solvents tend to be more expensive, thereby rendering the use of metal hydrides and amides less attractive for large scale industrial processing.

The $\alpha,\beta$-dihaloacrylonitrile derivative (IV) is slowly fed into the solution of the sulfur anion. The displacement reaction may be carried out at temperatures of 0°-80° C., the maximum operating temperature being limited by the boiling point of the reaction solvent and the boiling point of the mercaptan being used. Temperatures of 20°-50° C. are preferred, with the temperatures of 25°-35° C. being especially preferred.

Those compounds of formula I wherein X is chlorine are novel and are preferred in the practice of the present invention. The $\alpha$-chloro-$\beta$-(substituted)thioacrylonitriles exemplified herein including those wherein R is an alkyl, aryl, aralkyl, heterocyclic, or a thiocarbonyl group, all show broad spectrum activity toward fungi. Those derivatives wherein R is methyl or ethyl show a broad spectrum of activity against both fungi and bacteria and are especially preferred since they would be suitable for a wider variety of applications. While less preferred than the compounds wherein X is chlorine, the corresponding compounds wherein X is bromine show good activity. Those wherein R is methyl or ethyl show broad base activity against fungi and bacteria. Compounds wherein X is iodine would also be suitable.

The compounds of the invention may be added to aqueous systems or formulations that are susceptible to bacterial or fungal growth, either undiluted or dissolved in organic solvents such as alcohols, acetone, dimethylformamide and the like. They may be added alone or in combination with other biocides and/or functional compounds such as antioxidants, anticorrosive agents, surfactants, etc. Concentrations from about 0.001% to above 0.5% could be effectively used. Use of larger concentrations, while feasible, is recommended only for unusual applications. It is preferred to use concentrations from about 0.005% to about 0.2%. Concentrations are expressed as weight/volume, based on gran.s of compound of formula I in 100 ml of the aqueous system susceptible to microbial growth.

The compounds of this invention may also be used as preservatives for oil-in-water emulsions. A number of oil-in-water emulsions (e.g. cutting oils) are used in industry, for example in the high speed metal working and textile industries, for their cooling, lubricating, antistatic and anticorrosive properties. Unless adequately protected by an effective preservative, such systems are susceptible to bacterial decomposition producing obnoxious odors and potential health hazards. (Detailed descriptions of these systems, their microbiological problems and difficulties in their preservation can be found in E. O. Bennet, Soap Chem. Specialties 32, (1956) 46; F. W. Fabian et al., Applied Microbiology 1, (1953) 199-203.) In practicing the invention, the compound may be added by directly dissolving it in the concentrated oil which is then diluted with water to form the water/oil emulsion, or it may be added to the final emulsion either undiluted or dissolved in a solvent such as dimethylformamide, alcohol, acetone, etc. Similar methods known in the art for adding preservatives to such oil-in-water emulsions may also be used. There can be used as little as about 0.005%. Although amounts greater than 0.3% are operable, they are recommended only for unusual applications. It is preferred to use amounts in the range of from about 0.01% to about 0.20%, with amounts in the range of about 0.02% to 0.10% being especially preferred.

The compounds of this invention are effective and could be useful as cosmetic preservatives against the bacteria which spoil cosmetic formulations if they prove to be safe for human use. (Problems encountered in the preservation of cosmetics are described by A. P. Dunnigan, Drug and Cosmetic Industries 103, (1968) 43). If the compounds were found to be safe for human use and were used to protect cosmetic formulations, they may be added to the finished cosmetic product directly or dissolved in suitable solvents such as alcohol, acetone, dimethylformamide and the like. Alternatively the compounds may be dissolved in the oils or other raw materials used in the formula and then formulated in the final product. In cosmetic preparations, concentrations as low as 0.01% would be operable. Concentrations greater than 0.30%, while operable, would be recommended only for unusual applications. Concentrations in the range of from about 0.02% to about 0.20% would be preferred with concentrations of about 0.05% to 0.10% being especially preferred.

ILLUSTRATION OF THE PREFERRED EMBODIMENTS

A number of examples are provided herein to illustrate the preferred embodiments of this invention. They are included for the sole purpose of illustrating the preferred embodiments and should not be construed as limiting. They are intended to embrace any equivalents or obvious extensions which are known or should be known to one who is skilled in the art. These examples exemplify compounds of formula I wherein R is methyl, ethyl, propyl, butyl, p-chloro-phenyl, benzyl, thiazol-2-yl, benzothiazol-2-yl, and thiocarbamoyl.

EXAMPLE I

Synthesis of $\alpha,\alpha,\beta$-Trihalopropanonitriles, III a. $\alpha,\alpha,\beta$-Trichloropropanonitrile Acrylonitrile (150.0 g; 2.82 moles) is chlorinated with chlorine gas (>200.2 g; >5.64 moles) for approximately 8 hours. The reaction temperature is maintained at 25°-30° C. by external water cooling. The progress of the reaction is monitored by GLC analysis until essentially a single peak is obtained in the chromatogram. At this point, the flow of chlorine is discontinued and the reaction mixture is degassed by sparging with a vigorous nitrogen flow for one hour. The crude liquid product is distilled to yield 412.0 g (92%) of $\alpha,\alpha,\beta$-trichloropropanonitrile (bp 100° C. @ 125 mm Hg).

b. $\alpha,\alpha,\beta$-Tribromo-(and triiodo)-propanonitriles.

Using the procedure outlined in part a, acrylonitrile can be reacted with bromine to yield $\alpha,\alpha,\beta$-tribromopropanonitrile or with iodine to yield $\alpha,\alpha,\beta$-triiodopropanonitrile. (See K.C. Pande, U.S. Pat. No. 3,659,006, Apr. 25, 1972.)

EXAMPLE II

Synthesis of $\alpha,\beta$-Dihaloacrylonitriles, IV a. $\alpha,\beta$-Dichloroacrylonitrile Into a 500-mL reaction flask is charged $\alpha,\alpha,\beta$-trichloropropanonitrile (300.0 g; 1.89 moles) and quinoline (80.0 g; 0.62 mole). The mixture is stirred and heated at reflux (178° C.) for 8 hours. (The progress of the reaction is monitored by GLC analysis until essentially a single peak is obtained in the chromatogram.) At this point, the mixture is cooled and the product is isolated by fractional distillation to yield 204.0 g (88%) of $\alpha,\beta$-dichloroacrylonitrile (bp 70°-80° C. @125 mm Hg).

b. $\alpha,\beta$-Dibromoacrylonitrile

The $\alpha,\alpha,\beta$-tribromopropionitrile (263.6 g; 0.90 mole) is added to a 500-mL reaction flask and then 2,6-lutidine (146.5 g; 1.37 moles) is fed in slowly with stirring at such a rate so as to maintain the reaction temperature at 40° C. The mixture becomes very dark and a precipitate forms. Heat is then applied and the mixture stirred at 45°-50° C. for 2-3 hours. (Progress of the reaction is monitored by GLC.) The mixture is then cooled to room temperature, dissolved in 500 mL of ether, and the ether solution is washed once with water (250 mL), twice with 10%-HCl (200 mL each) and once with saturated sodium chloride solution (200 mL). The washed ether layer is dried over MgSO$_4$ or NaSO$_4$, filtered and concentrated on a rotary evaporator to yield 94.2 g of red oil. The red oil is distilled to yield 36.9 g (19%) of $\alpha,\beta$-dibromoacrylonitrile (bp 92°-95° C. @50 mm Hg) which is 95% pure by GLC.

EXAMPLE III

Synthesis of $\alpha$-Halo-$\beta$-(substituted)thioacrylonitriles, 1 a. $\alpha$-Bromo-$\beta$-methylthioacrylonitrile

Into a 250-mL reaction flask is added ethanol (50 mL) and sodium hydroxide (2.0 g; 0.05 mole). The mixture is stirred until the solid is completely dissolved and then methyl mercaptan gas (2.4 g; 0.05 mole) is slowly bubbled into the solution. A solution of $\alpha,\beta$-dibromoacrylonitrile (10.5 g; 0.05 mole) in ethanol (40 mL) is then added dropwise over 30 minutes at 25°-30° C. The resultant mixture is stirred at room temperature for 16 hours and is then concentrated under vacuum on a rotary evaporator.

The residual material is taken up into water (100 mL) and the aqueous mixture is extracted twice with 250-mL portions of ether. The combined ether extracts are washed once with saturated sodium chloride solution (50 mL), dried over magnesium sulfate, filtered and concentrated to yield 7.2 g of residual oil which is distilled to yield 2.3 g of $\alpha$-bromo-$\beta$-methylthioacrylonitrile (bp 84°-94° C. @ 1.5 mm Hg).

Analysis—Calculated for C$_4$H$_4$BrNS: C, 26.97; H, 2.26; N, 7.86. Found: C, 26.72; H, 2.60; N, 8.01.

b. General Procedure

Using procedures similar to the one outlined in part a and the appropriate mercaptan, one can prepare other compounds of formula I. The following table contains a number of representative derivatives. The spectral data (i.e., NMR, IR, etc.) were consistent with the assigned structures of the derivatives.

TABLE I $$X-CH=C\genfrac{}{}{0pt}{}{X}{CN} \xrightarrow{\text{RSH, Base}} RS-CH=C\genfrac{}{}{0pt}{}{X}{CN}$$

| Entry | RSH | X | Base | Solvent | Physical State | Boiling Point (°C./mm) | Melting Point (°C.) | | C | H | N | S | Halogen |
|---|---|---|---|---|---|---|---|---|---|---|---|---|---|
| 1 | CH₃SH | Cl | (C₂H₅)₃N | Glyme | Colorless Liquid | 66-69/1.0 | — | Calc'd Found | 35.96 35.92 | 3.02 3.11 | — — | — — | 26.54 26.31 |
| 2 | C₂H₅SH | Cl | (C₂H₅)₃N | Ethanol | Colorless Liquid | 74-76/2.0 | — | Calc'd Found | 40.68 40.95 | 4.10 4.32 | 9.49 9.54 | 21.72 21.92 | — — |
| 3 | C₂H₅SH | Br | NaOH | Ethanol | Colorless Liquid | 87-92/1.0 | — | Calc'd Found | 31.26 30.89 | 3.14 3.33 | 7.29 7.17 | — — | — — |
| 4 | n-C₃H₇SH | Cl | (C₂H₅)₃N | Ethanol | Colorless Liquid | 79-81/1.5 | — | Calc'd Found | 44.58 44.43 | 4.99 4.97 | 8.66 8.51 | 21.93 21.98 | — — |
| 5 | n-C₄H₉SH | Cl | NaOH | Ethanol | Colorless Liquid | 139-141/1.3 | — | Calc'd Found | 47.85 47.89 | 5.74 5.84 | 7.97 7.75 | 20.18 20.22 | — — |
| 6 | 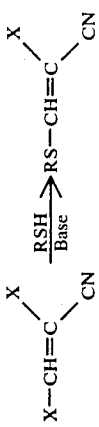 | Cl | NaOH | — | White Solid | 100/0.03 | — | Calc'd Found | 55.24 55.46 | 3.09 3.32 | — — | — — | 18.12 18.11 |
| 7 | 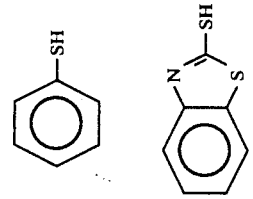 | Cl | NaOH | Ethanol | Light Tan Solid | — | 78-80ᵃ | Calc'd Found | 47.52 47.36 | 1.99 2.02 | 11.08 11.23 | — — | — — |
| 8 | 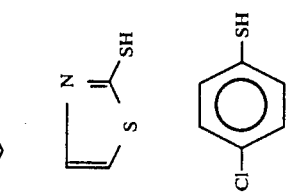 | Cl | NaOH | Water | Pale Green Solid | — | 43-53ᵃ | Calc'd Found | 35.55 35.62 | 1.49 1.50 | 13.82 13.92 | — — | 17.49 17.33 |
| 9 | 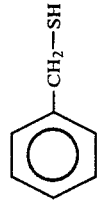 | Cl | NaOH | Ethanol/Water | White Solid | — | 112-114ᵇ | Calc'd Found | 46.97 46.72 | 2.19 2.11 | 6.09 5.99 | — — | 30.82 30.66 |
| 10 | C₆H₅CH₂—SH | Cl | (C₂H₅)₃N | Glyme | Liquid | 130-135/0.10 | — | Calc'd Found | 57.27 56.99 | 3.84 3.90 | 6.67 6.85 | — — | 15.29 15.40 |

Elemental Analysis

TABLE I-continued $$X-CH=C\begin{array}{c}X\\ \diagdown\\ CN\end{array}\xrightarrow[\text{Base}]{\text{RSH}}RS-CH=C\begin{array}{c}X\\ \diagdown\\ CN\end{array}$$

| Entry | RSH | X | Base | Solvent | Physical State | Boiling Point (°C./mm) | Melting Point (°C.) | | Elemental Analysis | | | | |
|-------|-----|---|------|---------|----------------|-----------------------|---------------------|---|---|---|---|---|---|
| | | | | | | | | | C | H | N | S | Halogen |
| 11 | (CH₃)₂N—C—SH (S=) | Cl | NaOH | Glyme/Water | Tan Solid | — | 97–100 | Calc'd<br>Found | 34.85<br>34.66 | 3.41<br>3.14 | 13.55<br>13.30 | 31.02<br>31.00 | 17.15<br>17.10 |

[a]sublimed
[b]from isopropanol

EXAMPLE IV

Illustration of General Antimicrobial Activity of α-Halo-β-(substituted) thioacrylonitrile Derivatives Antibacterial and antifungal activity were evaluated by a 5-fold serial dilution test in agar. In this test, compounds were prepared as 6% solutions in dimethylformamide (DMF) or ethanol. The 6% solution was then 5-fold serially diluted in test tubes to give the desired concentrations when mixed with agar and poured into sterile Petri dishes. Tryptone glucose extract agar was used for bacterial testing; mildew glucose agar for the fungal testing. The bacterial plates were spot inoculated with 24-hour nutrient broth cultures and incubated at 37° C. for 48 hours. The fungal plates were spot inoculated with spore suspensions and incubated at 28° C. for seven days. At the end of the incubation periods, all plates were examined for growth. The minimum inhibiting concentration (MIC) for each organism is expressed in Table II. In the ranges presented, growth is observed only in the lower concentration. The key to Table II is as follows:

| Activity Level | Growth @ mcg/ml | No Growth @ mcg/ml |
| --- | --- | --- |
| 0 | >1920 | — |
| 1 | 384 | 1920 |
| 2 | 76 | 384 |
| 3 | 15 | 76 |
| 4 | 3 | 15 |
| 5 | 0.6 | 3 |
| 6 | 0.12 | 0.6 |
| 7 | 0.03 | 0.12 |
| 8 | — | 0.03 |

| Microorganisms Tested | |
| --- | --- |
| Bacteria | Fungi |
| $B_1$ Staphylococcus aureus | $F_1$ Aspergillus niger |
| $B_2$ Escherichia coli | $F_2$ Aspergillus oryzae |
| $B_3$ Pseudomonas aeruginosa | $F_3$ Penicillium piscarium |
| $B_4$ Proteus vulgaris | $F_4$ Aureobasidium pullulans |

TABLE II $$RS-CH=C\begin{matrix}CN\\X-\end{matrix}$$

| Entry | R | X | Bacteria | | | | Fungi | | | |
| --- | --- | --- | --- | --- | --- | --- | --- | --- | --- | --- |
| | | | $B_1$ | $B_2$ | $B_3$ | $B_4$ | $F_1$ | $F_2$ | $F_3$ | $F_4$ |
| 1 | $CH_3$ | Cl | 4 | 4 | 4 | 5 | 5 | 5 | 5 | 4 |
| 2 | $CH_3$ | Br | 4 | 5 | 4 | 6 | 5 | 6 | 6 | 6 |
| 3 | $C_2H_5$ | Cl | 3 | 4 | 2 | 4 | 4 | 4 | 4 | 4 |
| 4 | $C_2H_5$ | Br | 4 | 5 | 3 | 6 | 6 | 6 | 6 | 5 |
| 5 | $n\text{-}C_3H_7$ | Cl | 3 | 3 | 0 | 3 | 4 | 3 | 4 | 4 |
| 6 | $n\text{-}C_4H_9$ | Cl | 3 | 0 | 0 | 3 | 3 | 3 | 3 | 3 |
| 7 | Phenyl | Cl | 6 | 4 | 1 | 5 | 6 | 6 | 5 | 5 |
| 8 | Cl—C$_6$H$_4$— | Cl | 6 | 0 | 0 | 2 | 7 | 7 | 6 | 4 |
| 9 | benzothiazol-2-yl | Cl | 6 | 0 | 0 | 1 | 5 | 7 | 5 | 5 |
| 10 | thiazol-2-yl | Cl | 4 | 3 | 1 | 4 | 5 | 6 | 4 | 5 |
| 11 | $C_6H_5$-$CH_2$— | Cl | 4 | 0 | 0 | 5 | 6 | 5 | 5 | 4 |
| 12 | $(CH_3)_2N\text{-}C(=S)-$ | Cl | 2 | 0 | 0 | 0 | 4 | 4 | 5 | 4 |

This example illustrates that all the compounds have broad spectrum activity against fungi. Those compounds wherein R is methyl or ethyl are also shown to have broad spectrum activity against bacteria.

EXAMPLE V

Applications a. Cutting Oil Emulsions

The efficacy of the acrylonitriles of formula I as preservatives for cutting oil emulsions was demonstrated by the following test.

Various aliquots of a 6% solution of the test compound in ethanol were added to cutting oil emulsions prepared by diluting Kutwell 30 cutting oil concentrate 1 to 30 with water. These samples were inoculated with a culture of Ps. aeruginosa and incubated at 28° C. on a rotary shaker. At weekly intervals, the samples were examined for microorganisms and then reinoculated and incubated. Results are tabulated in Table III.

Samples of the lotion containing varying levels of the acrylonitrile derivatives were divided into two por-

TABLE III $$RS-CH=C\begin{array}{c}CN\\ \diagdown\\ X-\end{array}$$

| | | | Minimum Inhibitory Concentration (ppm)[a] Incubation Period (Weeks) | | | |
|---|---|---|---|---|---|---|
| Entry | R | X | 1 | 2 | 3 | 4 |
| 1 | $CH_3$ | Cl | 1.95–3.9 | 1.95–3.9 | 1.95–3.9 | 3.9–7.8 |
| 2 | $CH_3$ | Br | <0.98 | 0.98–1.95 | 7.8–15 | 15–31 |
| 3 | $C_2H_5$ | Cl | 15–31 | 15–31 | 15–31 | 31–62 |
| 4 | $C_2H_5$ | Br | 3.9–7.8 | 3.9–7.8 | 15–31 | 31–62 |
| 5 | $n\text{-}C_3H_7$ | Cl | 125–250 | 62.5–125 | 125–250 | 125–250 |
| 6 | $n\text{-}C_4H_9$ | Cl | >500 | — | — | — |
| 7 | Phenyl | Cl | 250–500 | 250–500 | 250–500 | 125–250 |
| 8 | Cl–C₆H₄– | Cl | >500 | — | — | — |
| 9 | benzothiazol-2-yl | Cl | >500 | — | — | — |
| 10 | thiazol-2-yl | Cl | 125–250 | >500 | >500 | >500 |
| 11 | $C_6H_5\text{-}CH_2\text{-}$ | Cl | >500 | — | — | — |
| 12 | $(CH_3)_2N-C(=S)-$ | Cl | >500 | — | — | — |

[a]Concentrations tested were 0.98 ppm, 1.95, 3.9, 7.8, 15, 31, 62, 125, 250 and 500 ppm.

This test shows that those derivatives wherein R is methyl or ethyl are highly effective in inhibiting bacterial growth in cutting oil emulsions.

b. Cosmetic Compositions

The efficacy of the acrylonitriles of formula I as preservatives in cosmetic compositions was demonstrated by the following test.

Serial dilutions of the compounds in dimethylformamide (DMF) were added to a prepared, sterile cosmetic lotion of the following composition:

| Ingredients | Parts by Weight |
|---|---|
| Stearic Acid | 1.4 |
| Mineral Oil | 2.3 |
| Arlacel-60 (sorbitan monostearate) | 0.7 |
| Tween-60 (polyoxyethylene sorbitan monostearate) | 1.6 |
| Distilled Water | 94.0 |
| Total | 100.0 parts | tions; one portion was inoculated with a spore suspension of *A. niger*, and the other portion with a 24-hour nutrient broth culture of *Ps. aeruginosa*. These two organisms are frequently found as contaminants in cosmetic products. The samples were incubated for a 4-week period with weekly examinations for the growth of the organisms. At weekly intervals, the samples were also reinoculated with the test organisms. Presence of fungal growth was determined macroscopically while bacteria contamination was determined by streaking one 4-mm loopful (0.01 ml.) of the lotion onto the surface of trypticase glucose extract agar (Baltimore Biological Laboratories, Baltimore, MD) containing 0.005% triphenyl tetrazolium chloride and letheen antidote. Results of these tests showing the minimum inhibitory concentration (MIC) through the 4-week incubation period are tabulated in Table IV and show, once again, that the compounds where R is methyl or ethyl show a broad spectrum activity for the preservation of cosmetic products against the type of fungus and bacterium most likely to cause problems in cosmetics.

TABLE IV $$RS-CH=C\begin{subarray}{c}CN\\X\end{subarray}$$

| Entry | R | X | Organism[a] | Minimum Inhibitory Concentration (ppm)[b] | | | |
|---|---|---|---|---|---|---|---|
| | | | | Week 1 | Week 2 | Week 3 | Week 4 |
| 1 | CH$_3$ | Cl | P.a. | 31–62 | 15–31 | 15–31 | 15–31 |
| | | | A.n. | <7.8 | <7.8 | <7.8 | <7.8 |
| 2 | CH$_3$ | Br | P.a. | <7.8 | <7.8 | <7.8 | <7.8 |
| | | | A.n. | <7.8 | <7.8 | <7.8 | <7.8 |
| 3 | C$_2$H$_5$ | Cl | P.a. | 250–500 | 125–250 | 125–250 | 125–250 |
| | | | A.n. | <7.8 | <7.8 | <7.8 | <7.8 |
| 4 | C$_2$H$_5$ | Br | P.a. | 31–62 | 31–62 | 31–62 | 31–62 |
| | | | A.n. | <7.8 | <7.8 | <7.8 | <7.8 |
| 5 | n-C$_3$H$_7$ | Cl | P.a. | >2000 | 1000–2000 | 1000–2000 | 500–1000 |
| | | | A.n. | 125–250 | 125–250 | 125–250 | 125–250 |
| 6 | n-C$_4$H$_9$ | Cl | P.a. | >2000 | — | — | — |
| 7 | Phenyl | Cl | P.a. | >2000 | >2000 | 1000–2000 | 1000–2000 |
| | | | A.n. | 250–500 | 250–500 | 250–500 | 250–500 |
| 8 | Cl-C$_6$H$_4$- | Cl | P.a. | >2000 | — | — | — |
| 9 | benzothiazol-2-yl | Cl | P.a. | >2000 | — | — | — |
| 10 | thiazolyl | Cl | P.a. | 1000–2000 | 1000–2000 | 1000–2000 | 1000–2000 |
| | | | A.n. | <125 | <125 | <125 | <125 |
| 11 | C$_6$H$_5$CH$_2$– | Cl | P.a. | >2000 | — | — | — |
| 12 | (CH$_3$)$_2$N–C(=S)– | Cl | P.a. | >2000 | — | — | — |

[a] P.a. is *Pseudomonas aeruginosa* A.n. is *Aspergillus niger*
[b] Concentrations tested were 7.8 ppm, 15, 31, 62, 125, 250, 500, 1000 and 2000 ppm.

We claim:

1. A method of controlling fungal and/or bacterial growth in an aqueous composition subject to spoilage thereby, which comprises incorporating in said composition an effective amount of a compound of the formula $$RS-CH=C\begin{subarray}{c}CN\\X\end{subarray}\qquad I$$

wherein R represents methyl, ethyl, propyl or butyl and X is chlorine or bromine.

2. A method according to claim 1 wherein R is methyl or ethyl.

3. The method according to claim 2 wherein the compound is α-chloro-β-methylthioacrylonitrile.

4. The method according to claim 2 wherein the compound is α-chloro-β-ethylthioacrylonitrile.

5. The method according to claim 2 wherein the compound is α-bromo-β-methylthioacrylonitrile.

6. The method according to claim 3 wherein the compound is α-bromo-β-ethylthioacrylonitrile.

* * * * *

UNITED STATES PATENT AND TRADEMARK OFFICE
CERTIFICATE OF CORRECTION

PATENT NO. : 5,039,702

DATED : August 13, 1991

INVENTOR(S) : A. Brandman (Executrix), M. Manowitz

It is certified that error appears in the above-identified patent and that said Letters Patent is hereby corrected as shown below:

On the title page, section [75] Inventors, delete "Albert I. Rachlin, Verona".

On the title page, section [56] References Cited, under U.S. PATENT DOCUMENTS, correct "4,238,408" to read --4,238,405--.

Column 11 and 12, Table II, and at column 13 and 14, Table III, correct $$" \quad RS - CH - C \begin{array}{c} \diagup CN \\ \diagdown X^- \end{array} \quad "$$

to read $$-- \quad RS - CH - C \begin{array}{c} \diagup CN \\ \diagdown X \end{array} \quad --$$

Signed and Sealed this

Second Day of March, 1993

*Attest:*

STEPHEN G. KUNIN

*Attesting Officer*     *Acting Commissioner of Patents and Trademarks*